United States Patent
Taniguchi et al.

(10) Patent No.: US 7,189,373 B2
(45) Date of Patent: Mar. 13, 2007

(54) CARBON MONOXIDE REMOVAL FROM REFORMATE GAS

(75) Inventors: Ikuhiro Taniguchi, Zushi (JP); Hiroaki Hashigaya, Yokohama (JP)

(73) Assignee: Nissan Motor Co., Ltd., Kanagwa (JP)

(*) Notice: Subject to any disclaimer, the term of this patent is extended or adjusted under 35 U.S.C. 154(b) by 537 days.

(21) Appl. No.: 10/367,755

(22) Filed: Feb. 19, 2003

(65) Prior Publication Data

US 2003/0185709 A1 Oct. 2, 2003

(30) Foreign Application Priority Data

Mar. 27, 2002 (JP) ............... 2002-088058

(51) Int. Cl.
- B01J 10/00 (2006.01)
- B01J 10/02 (2006.01)
- B01J 12/00 (2006.01)
- B01J 12/02 (2006.01)
- B01J 14/00 (2006.01)

(52) U.S. Cl. .............. 422/129; 429/12; 429/13; 422/101; 436/145; 436/147; 436/155; 436/157; 436/159; 436/160; 436/174; 436/175; 436/177

(58) Field of Classification Search ............ 436/145, 436/147, 155, 157, 159, 160, 174, 175, 177; 422/101, 129; 429/12, 13
See application file for complete search history.

(56) References Cited

U.S. PATENT DOCUMENTS

| | | | |
|---|---|---|---|
| 4,046,956 A | 9/1977 | Fanciullo | |
| 6,010,675 A | 1/2000 | Trocciola et al. | |
| 6,245,214 B1 * | 6/2001 | Rehg et al. | 205/764 |
| 6,403,049 B1 * | 6/2002 | Van Keulen et al. | 423/247 |
| 6,752,968 B2 * | 6/2004 | Hashigaya et al. | 422/110 |
| 6,786,942 B2 * | 9/2004 | Ichikawa | 48/76 |
| 6,916,564 B2 * | 7/2005 | Clawson et al. | 429/17 |
| 6,921,595 B2 * | 7/2005 | Clawson et al. | 429/17 |
| 2001/0014300 A1 * | 8/2001 | Hashigaya et al. | 422/195 |
| 2001/0037948 A1 * | 11/2001 | Liu et al. | 205/555 |
| 2004/0047788 A1 * | 3/2004 | Abe | 423/247 |

FOREIGN PATENT DOCUMENTS

| | | |
|---|---|---|
| DE | 100 01 167 A1 | 7/2000 |
| EP | 0 941 963 A1 | 9/1999 |
| EP | 0 995 717 A1 | 4/2000 |
| JP | 08-329969 | 12/1996 |
| JP | 2000-154002 A | 6/2000 |
| JP | P2000-169106 A | 6/2000 |
| JP | 2000-188122 A | 7/2000 |
| JP | P2002-234707 A | 8/2002 |

* cited by examiner

*Primary Examiner*—Brian Sines
(74) *Attorney, Agent, or Firm*—McDermott Will & Emery LLP

(57) ABSTRACT

Carbon monoxide contained in reformate gas is removed by a preferential oxidation reaction in a catalyst, two preferential oxidation reactors (20A, 20B) being disposed in series. Valves (7, 8) supply air containing oxygen as an oxidizing agent individually to these preferential oxidation reactors (20A, 20B). Temperature sensors (9, 10) detect the catalyst temperatures of the preferential oxidation reactors (20A, 20B), and a controller (5), by adjusting the flow rate of the valves (7, 8) based on the detected temperatures, maximizes the carbon monoxide removal performance of the preferential oxidation reactors (20A, 20B), while preventing excessive catalyst temperature rise.

7 Claims, 13 Drawing Sheets

CARBON MONOXIDE REMOVAL FROM REFORMATE GAS

FIELD OF THE INVENTION

This invention relates to the removal of carbon monoxide from reformate gas used in a fuel cell power plant.

BACKGROUND OF THE INVENTION

In fuel cell power plants using reformate gas, it is necessary to remove carbon monoxide from the reformate gas generated by a reformer. In JP2000-169106 published by the Japanese Patent office in 2000, a carbon monoxide oxidizer is disclosed. The carbon monoxide oxidizer comprises two preferential oxidation reactors (PROX reactors) which are arranged in series. A catalyst comprising a noble metal is disposed inside the preferential oxidation reactors. Air is respectively supplied to the PROX reactors, and the catalyst removes CO in the reformate gas by reacting the CO in the reformate gas with oxygen ($O_2$) in the air to produce carbon dioxide ($CO_2$).

JP08-329969 published by the Japanese Patent Office in 1996 discloses a method where the reaction amount of the PROX reactor is controlled by increasing the air supply amount to the PROX reactor according to the increase in the CO concentration in the reformate gas.

SUMMARY OF THE INVENTION

The preferential oxidation reaction is an exothermic reaction, and when the air supply amount to the PROX reactor is increased, the liberated heat increases as the preferential oxidation reaction proceeds, so the temperature of the catalyst rises. As a result, if the catalyst temperature increases above the reaction temperature of the catalyst, the catalyst deteriorates.

The two PROX reactors in the carbon monoxide removal system of JP2000-169106 are respectively cooled by a coolant, but as described in JP08-329969, when the air supply amount is increased according to the CO concentration in the reformate gas, it can be expected that the temperature rise of the catalyst will easily exceed the cooling ability of the coolant.

It is therefore an object of this invention to make optimum use of carbon monoxide removal performance while preventing excessive catalyst temperature rise in a carbon monoxide removal system comprising plural PROX reactors disposed in series.

In order to achieve the above object, this invention provides a carbon monoxide removal system comprising plural PROX reactors disposed in series which remove carbon monoxide contained in reformate gas via a catalyst, wherein the PROX reactors comprises a first PROX reactor and a second PROX reactor arranged further downstream than the first PROX reactor. The system further comprises an air supply mechanism which supplies air containing oxygen as an oxidizing agent to the first PROX reactor and the second PROX reactor, a first temperature sensor which detects a temperature of the first PROX reactor, a second temperature sensor which detects a temperature of the second PROX reactor, and a controller functioning to control the air supply mechanism so that an air supply flow rate to the first PROX reactor and an air supply flow rate to the second PROX reactor vary based on the temperature of the first PROX reactor and the temperature of the second PROX reactor.

This invention also provides a control method of a carbon monoxide removal system comprising plural PROX reactors disposed in series which remove carbon monoxide contained in reformate gas via a catalyst, wherein the PROX reactors comprises a first PROX reactor and a second PROX reactor arranged further downstream than the first PROX reactor. The method comprises supplying air to the first PROX reactor and the second PROX reactor, detecting a temperature of the first PROX reactor, detecting a temperature of the second PROX reactor, and varying an air supply flow rate to the second PROX reactor and an sir supply flow rate to the second PROX reactor based on the temperature of the first PROX reactor and the temperature of the second PROX reactor.

The details as well as other features and advantages of this invention are set forth in the remainder of the specification and are shown in the accompanying drawings.

DESCRIPTION OF THE PREFERRED EMBODIMENTS

Figure 1:
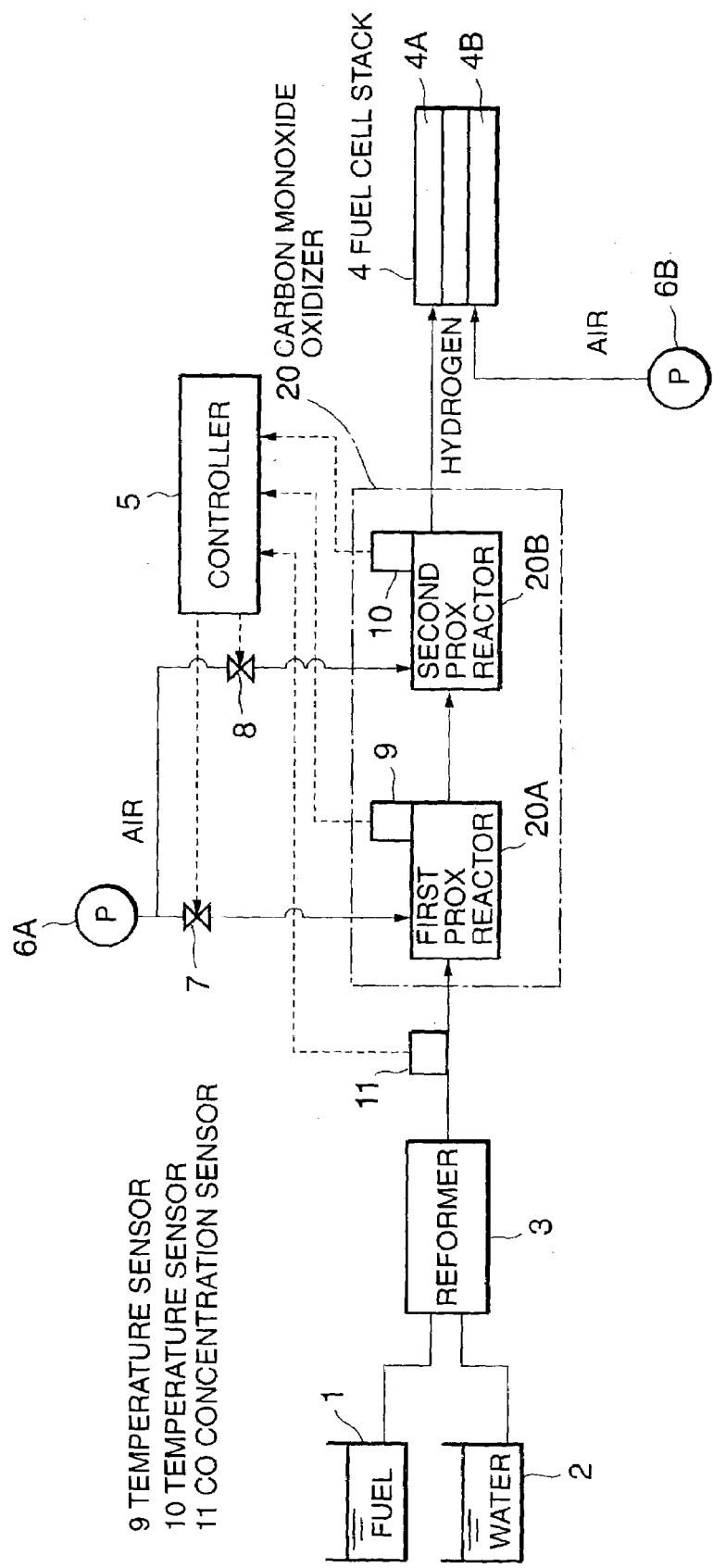
FIG. 1 is a schematic diagram of a fuel cell power plant comprising a carbon monoxide removal system according to this invention.

Referring to FIG. 1 of the drawings, a fuel cell power plant for a vehicle removes carbon monoxide in reformate gas produced by a reformer 3 by a carbon monoxide oxidizer 20 comprising two PROX reactors 20A, 20B, and supplies an anode 4A of a fuel cell stack 4 with hydrogen-rich gas. Air is supplied from an air pump 6B to a cathode 4B of the fuel cell stack 4. The hydrogen-rich gas and the oxygen in the air cause electrode reactions shown by the following chemical equations (1), (2) at the anode 4A and cathode 4B.

$$\text{Anode } 4A: H_2 \rightarrow 2H^+ + 2e^- \tag{1}$$

$$\text{Cathode } 4B: 2H^+ + 2e^- + \frac{1}{2}O_2 \rightarrow H_2O \tag{2}$$

Due to the power generated by these electrode reactions, the fuel cell stack 4 generates power. A vehicle drive motor, not shown, is connected to the fuel cell stack 4.

Fuel gas from a fuel tank 1 and water from a water tank 2 are respectively supplied to the reformer 3. The fuel gas may be a hydrocarbon fuel such as methanol or gasoline.

If methanol is used as the fuel gas, the reformer 3 generates reformate gas according to the chemical reactions shown by the following chemical equations (3), (4).

$$CH_3OH + H_2O \rightarrow CO_2 + 3H_2 \tag{3}$$

$$CH_3OH \rightarrow CO + 2H_2 \tag{4}$$

The reformate gas has hydrogen (H) as its main component, and contains carbon monoxide (CO). If the carbon monoxide is supplied to the fuel cell stack 4, it causes a decline of power generating efficiency of the fuel cell stack 4, and poisons the catalyst at the anode 4A of the fuel cell stack 4. Therefore, the carbon monoxide in the reformate gas is removed by the carbon monoxide oxidizer 20, and hydrogen-rich gas in which the carbon monoxide concentration has been sufficiently reduced is supplied to the anode of the fuel cell stack 4.

The preferential oxidation reaction which takes place in the first PROX reactor 20A and second PROX reactor 20B of the carbon monoxide oxidizer 20, may be represented by the following chemical equation (5).

$$CO + \frac{1}{2}O_2 \rightarrow CO_2 \tag{5}$$

Due to equation (5), the carbon monoxide oxidizer 20 decreases the CO concentration in the reformate gas from the order of several percent to about 100 ppm in the first PROX reactor 20A, and then from about 1000 ppm to less than 20 ppm in the second PROX reactor 20B.

The oxygen ($O_2$) required for the preferential oxidation reaction is respectively supplied as air to the first PROX reactor 20A via a valve 7, and to the second PROX reactor 20B via a valve 8. The air pump 6A has a function to supply air constantly under a constant pressure.

Therefore, the air supply flow rate to the first PROX reactor 20A is determined by the opening of the valve 7. Likewise, the old air supply flow rate to the second PROX reactor 20B is determined by the opening of the valve 8.

The valves 7, 8 comprise electro-magnetic valves of which the opening is varied according to opening signals respectively output by the controller 5.

The controller 5 controls the opening of the valves 7, 8 depending on the carbon monoxide concentration in the reformate gas and the temperatures of the first PROX reactor 20A and second PROX reactor 20B. The first PROX reactor 20A and second PROX reactor 20B have identical specifications.

For this purpose, a CO concentration sensor 11 which detects the carbon monoxide concentration in the reformate gas produced by the reformer 3 is installed midway in a pipe leading reformate gas from the reformer 3 to the carbon monoxide oxidizer 20. Also, a temperature sensor which detects the catalyst temperature of the first PROX reactor 20A and a temperature sensor 10 which detects the catalyst temperature of the second PROX reactor 20B, are provided. The detection data from these sensors are respectively input to the controller 5 as signals.

The controller 5 comprises a microprocessor having a central processing unit (CPU), read-only memory (ROM), random access memory (RAM) and input/output interface (I/O interface). The controller may also comprise plural microcomputers.

When the temperature or pressure in the reformer 3 varies, the CO concentration in reformate gas may rise above the CO concentration in the normal running state. In such a case, the air supply flow rate to the PROX reactors 20A, 20B must be increased so that the CO concentration in the hydrogen-rich gas supplied to the fuel cell stack 4 does not increase, and the carbon monoxide removal efficiency is enhanced.

However, when the air supply flow rate to the PROX reactors 20A, 20B is increased, the catalyst temperature rises due to the preferential oxidation reaction which is an exothermic reaction, and the catalyst may deteriorate. The controller 5 therefore, when the catalyst temperature is lower than the predetermined temperature, opens the valves 7, 8 to increase the air supply flow rate to the PROX reactors 20A, 20B, and when the catalyst temperature is higher than the predetermined temperature, it closes the valves 7, 8 to decrease the air supply flow rate to the PROX reactors 20A, 2B.

Next, referring to FIG. 2, a routine of controlling the air supply flow rate executed by the controller 5 to perform this control will be described. This routine is executed at an interval of 0.1 seconds during the running of the fuel cell power plant. The routines for controlling the air supply flow rate according to other embodiments described later, are all repeatedly executed at an interval of 0.1 seconds during the running of the power plant.

First, the controller 5, in a step S11, reads the temperature detected by the temperature sensor 9, in a step S12, reads the temperature detected by the temperature sensor 10, and in a step S13, reads the temperature detected by the CO concentration sensor 11.

In a following step S14, the detected CO concentration in the reformate gas is compared with a preset specified concentration. From the allowable CO concentration in the hydrogen-rich gas supplied to the fuel cell stack 4, and the CO removal performance of the PROX reactors 20A, 20B during normal running, the allowable CO concentration in the reformate gas can be calculated. The specified concentration is a value set based on the allowable CO concentration. A typical specified concentration range is 1–2%.

When the CO concentration in the reformate gas is lower than the specified concentration, the controller 5 immediately terminates the routine without proceeding to subsequent steps. This is because, in this case, the CO concentration in the hydrogen-rich gas remains within the allowable range even if the air supply flow rate to the PROX reactors 20A, 20B is not increased.

When the CO concentration in the reformate gas is not lower than the specified concentration, in a step S15, the controller 5 compares the catalyst temperature of the first PROX reactor 20A with a predetermined temperature. The predetermined temperature is set to a value within the activation temperature range of the catalyst. A typical predetermined temperature is within the range of 140° C. to 160° C.

When the catalyst temperature of the first PROX reactor 20A is not lower than the predetermined temperature, in a step S16, the controller 5 throttles the valve 7 by a fixed amount. Due to this processing, as the air flow rate supplied to the first PROX reactor 20A decreases, the preferential oxidation reaction amount in the first PROX reactor 20A decreases, and the catalyst temperature correspondingly decreases. After the processing of the step S16, the controller 5 performs the processing of a step S18.

When the catalyst temperature of the first PROX reactor 20A is lower than the predetermined temperature, the controller 5 performs the processing of a step S17.

Figure 3:
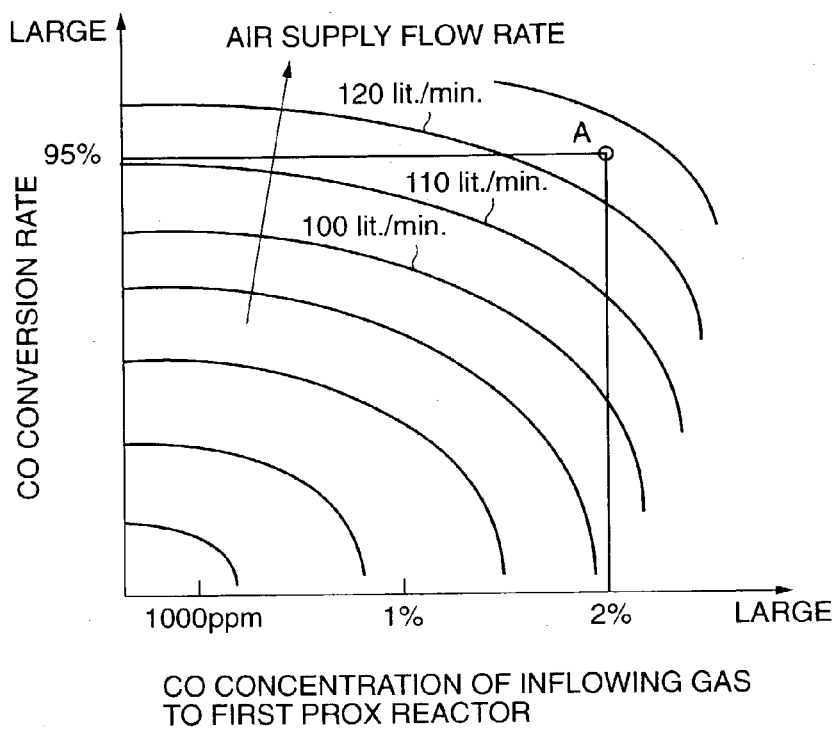
FIG. 3 is a diagram showing the relation between carbon monoxide concentration in reformate gas flowing into a first PROX reactor, air supply flow rate and carbon monoxide conversion rate of the first PROX reactor.

In the step S17, a map having the characteristics shown in FIG. 3 prestored in a memory is looked up, and the air flow rate required to reach a target CO conversion rate is calculated from the CO concentration in the reformate gas. A typical target CO conversion rate is 95%.

Referring to FIG. 3, when the CO concentration in reformate gas is for example 2%, in order for the first PROX reactor 20A to reach the CO conversion rate of 95%, an air supply flow rate of 120 liter/minute corresponding to a point A is required. The controller 5 adjusts the opening of the valve 7 so that the air flow rate calculated in this way is realized.

The controller 5 further calculates the CO concentration in the gas flowing from the first PROX reactor 20A by the following equation (6):

$$\text{CO concentration in outflowing gas} = (1 - \text{CO conversion rate}) \cdot \text{CO concentration in inflowing gas} \quad (6)$$

Calculating the CO concentration flowing from the first PROX reactor 20A using equation (6) when the CO concentration in the inflowing gas is 2% and the CO conversion rate is 95% as described above, the calculation results shown by the following equation (7) are obtained:

$$\text{CO concentration in outflowing gas} = (1-0.95) \cdot 2\% = 0.1\% = 1{,}000 \text{ ppm} \quad (7)$$

After the opening of the valve 7 is adjusted in the step S16 or 17, in the step S18, the controller 5 compares the catalyst temperature of the second PROX reactor 20B with the aforesaid predetermined temperature. According to this embodiment, a common predetermined temperature is used in the steps S15 and S18, but different predetermined temperatures may also be used for catalysts having different activities in the first PROX reactor 20A and second PROX reactor 20B.

When the catalyst temperature of the second PROX reactor 20B is not lower than the predetermined temperature, in a step S19, the controller 5 throttles the opening of the valve 8 by a fixed amount. Due to this processing, as the air flow rate supplied to the second PROX reactor 20B decreases, the preferential oxidation reaction amount in the second PROX reactor 20B decreases, and the catalyst temperature decreases correspondingly. After the processing of the step S19, the controller 5 terminates the routine.

When the catalyst temperature of the second PROX reactor 20B is lower than the predetermined temperature, the controller 5 performs the processing of a step S20.

In the step S20, the air flow rate required to reach the target CO conversion rate is calculated from the CO concentration of the inflowing gas by looking up the map having the characteristics shown in FIG. 3 which was looked up in the step S17. As described above, the first PROX reactor 20A and second PROX reactor 20B have identical specifications, so the same map can be used in the steps S17 and S20, but if the specifications of the first PROX reactor 20A and second PROX reactor 20B are different, different maps are used. Here, the CO concentration in the inflowing gas is the CO concentration in the gas flowing out of the first PROX reactor 20A calculated in the equation (7). The controller 5 adjusts the opening of the valve 8 to realize the air flow rate thus obtained, in a next step S21. After the processing of the step S21, the controller 5 terminates the routine.

As a result of executing the above routine, when the CO concentration in the reformate gas rises, the air flow rates supplied to the first PROX reactor 20A and second PROX reactor 20B increase until the catalysts in the first PROX reactor 20A and second PROX reactor 20B reach the predetermined temperature, and the CO removal performance of the first PROX reactor 20A and second PROX reactor 20B are enhanced. On the other hand, when either one of catalyst temperatures of the first PROX reactor 20A and second PROX reactor 20B is not lower than the predetermined temperature, the catalyst temperature of the corresponding PROX reactor is reduced to the predetermined temperature by decreasing the air flow rate supplied to that PROX reactor.

Therefore, by executing this routine, in a carbon monoxide oxidizer comprising plural PROX reactors arranged in series, the carbon monoxide removal performance can be optimized while preventing rise of catalyst temperature in the PROX reactors.

Next, referring to FIG. 4, a second embodiment of this invention will be described.

The hardware construction of this embodiment is identical to that of the first embodiment. In this embodiment, only the routine for controlling the air supplier flow rate performed by the controller 5 is different from that of the first embodiment as shown by FIG. 4.

In this embodiment, the air flow rate is determined based on a difference between the upper limiting temperature for catalyst activation of the first PROX reactor 20A and second PROX reactor 20B, and the detected catalyst temperatures. The openings of the valves 7, 8 are adjusted correspondingly.

The upper limiting temperature for catalyst activation is the highest value within the temperature range when the catalyst is activated. A typical upper limiting temperature for catalyst activation is within the range of 200° C.–240° C. According to this embodiment, a common upper limiting temperature for catalyst activation is used for the first PROX reactor 20A and second PROX reactor 20B, but when different catalysts are used in the first PROX reactor 20A and second PROX reactor 20B, different upper limiting temperatures for catalyst activation are used according to the characteristics of these catalysts.

The processing of the steps S11–S14 is identical to that of the first embodiment. In the step S14, when the CO concentration of the reformate gas is not lower than the specified concentration, the controller 5 performs the processing of a step S31. In the step S14, when the CO concentration of the reformate gas is lower than the specified concentration, the controller 5 immediately terminates the routine.

In the step S31, the controller 5 calculates a temperature difference $\Delta T1$ between the upper limiting temperature for catalyst activation and the temperature of the first PROX reactor 20A.

In a following step S32, the controller 5 calculates a temperature difference $\Delta T2$ between the upper limiting temperature for catalyst activation and the temperature of the second PROX reactor 20B.

In a following step S33, it is determined whether or not one of the temperature difference $\Delta T1$ and temperature difference $\Delta T2$ is a negative value. When one of these values is a negative value, in a step S34, the controller 5 throttles the opening of the valve of the PROX reactor for which the temperature difference was a negative value by a fixed amount. After the processing of the step S34, the controller 5 terminates the routine.

When, in the step S33, neither of the temperature differences are negative values, in a step S35, the controller 5 compares the temperature difference $\Delta T1$ and temperature difference $\Delta T2$. When the temperature difference $\Delta T1$ is larger than the temperature difference $\Delta T2$, in a step S38, the controller 5 looks up the map having the characteristics shown in FIG. 3 prestored in the memory, and calculates the air flow rate required to reach the target CO conversion rate from the CO concentration detected by the CO concentration sensor 11. This calculation is identical to the calculation of the step S17 of the routine of FIG. 2 according to the first embodiment. Further, the controller 5 adjusts the opening of the valve 7 so that the calculated air flow rate is realized.

On the other hand, when the temperature difference $\Delta T1$ is not larger than the temperature difference $\Delta T2$, the controller 5 continuously performs the processing of steps S36 and S37.

In the step S36, the controller 5 calculates the CO concentration of the gas flowing into the second PROX reactor 20B. To do this, the controller 5 first calculates the CO conversion rate of the first PROX reactor 20A by looking up the map having the characteristics shown in FIG. 3 from the CO concentration detected by the CO concentration sensor 11 and the air flow rate supplied to the first PROX reactor 20A. Next, the CO concentration of the outflowing gas is calculated by substituting the CO concentration detected by the CO concentration sensor 11 and the CO conversion rate obtained into equation (6). This is effectively the CO concentration of the gas flowing into the second PROX reactor 20B.

In the step S37, the controller 5 adjusts the air flow rate required to reach the target CO conversion rate by looking up the map having the characteristics shown in FIG. 3 from the CO concentration of the gas flowing into the second PROX reactor 20B. The controller 5 further adjusts the opening of the valve 8 to realize the calculated air flow rate. After the processing of the step S37, the controller 5 terminates the routine.

Due to the processing of this routine, when the CO concentration of the reformate gas is not lower than the specified concentration, the controller 5 determines whether or not the catalyst temperature of one of the PROX reactors exceeds the upper limiting temperature for catalyst activation, and when it does exceed this temperature, the air supply flow rate to the corresponding PROX reactor is reduced.

On the other hand, when neither of the catalyst temperatures of the PROX reactors exceeds the upper limiting temperature for catalyst activation, the air supply flow rate to the PROX reactor which is at a relatively low temperature, i.e. the PROX reactor which has more tolerance for temperature rise, is increased. Therefore, the carbon monoxide removal performance can be optimized while effectively preventing rise in the catalyst temperatures of the PROX reactors.

Next, referring to FIGS. 5, 6, a third embodiment of this invention will be described.

The hardware construction of this embodiment is identical to that of the first and second embodiments. In this embodiment, only the routine for controlling the air supply flow rate executed by the controller 5 shown in FIG. 5 is different from those of the first and second embodiments.

Figure 6:
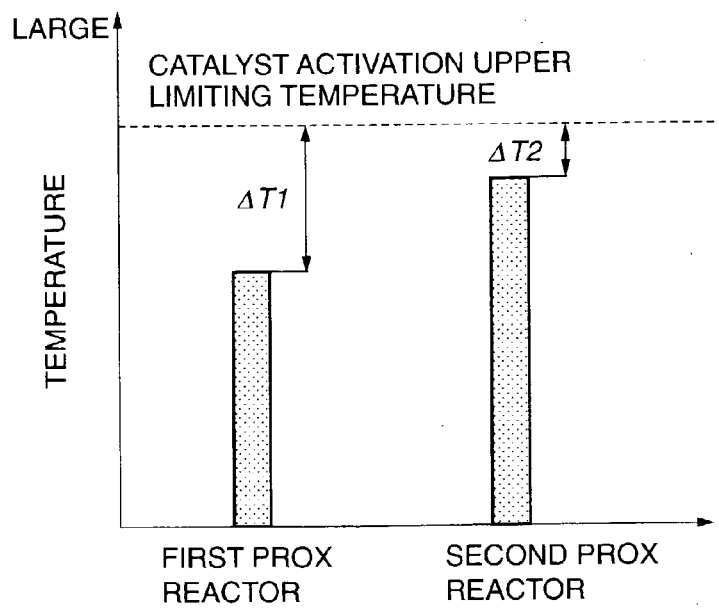
FIG. 6 is a diagram describing differences $\Delta T1$, $\Delta T2$ between the catalyst temperatures of PROX reactors and the catalyst activation upper limiting temperatures calculated by the controller according to a third embodiment of this invention.

In this embodiment, increments of the CO conversion rates are determined based on the temperature differences $\Delta T1$, $\Delta T2$ between the upper limiting temperature for catalyst activation and the catalyst temperatures of the PROX reactors as shown in FIG. 6, and the air supply flow rate to the PROX reactors is determined based on the determined increments.

Figure 5:
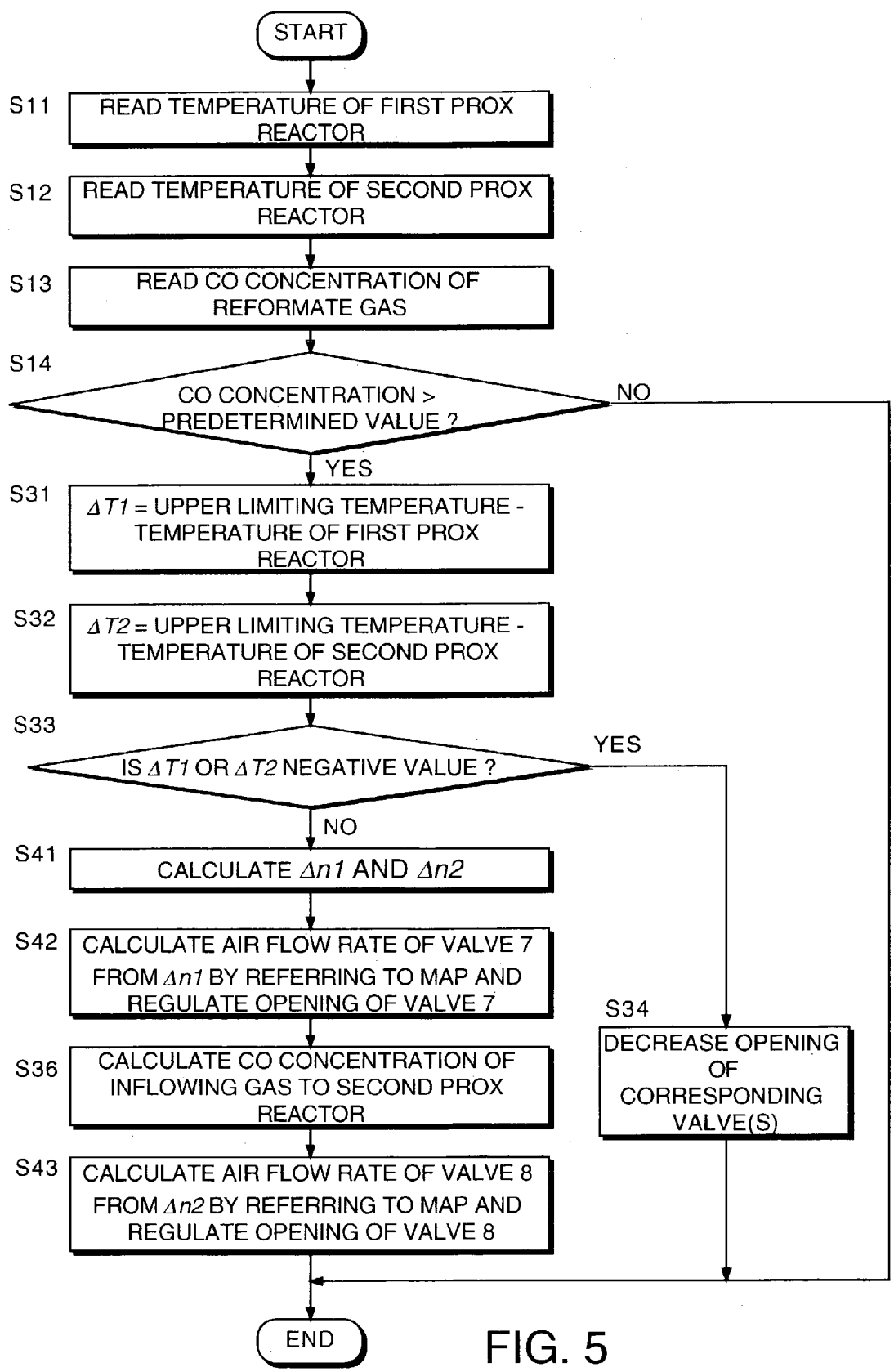
FIG. 5 is similar to FIG. 2, but showing a third embodiment of this invention.

Referring to FIG. 5, the processing of the steps S11 to S14 and steps S31 to S34 is identical to that of the second embodiment.

In the step S33, the controller 5, when neither of the temperature differences $\Delta T1$, $\Delta T2$ are negative values, i.e., when both of them are positive values, the processing of steps S41 to S43 is performed.

In the step S41, the controller 5 increases the CO conversion rates of the first PROX reactor 20A and second PROX reactor 20B respectively in the proportion of $\Delta T1 : \Delta T2$ from the target CO conversion rate. In this embodiment, let the target CO conversion rate of the first PROX reactor 20A be 95%, and the target CO conversion rate of the second PROX reactor 20B be 98%. Also, let the target CO concentration of hydrogen-rich gas flowing from the second PROX reactor 20B be 20 ppm.

Increments $\Delta n1$, $\Delta n2$ in the CO conversion rate of the first PROX reactor 20A and second PROX reactor 20B, have the relationship of the following equation (8):

$$\Delta n1 : \Delta n2 = \Delta T1 : \Delta T2 \tag{8}$$

The following equation (9) is obtained from equation (8):

$$\Delta n1 \cdot \Delta T2 = \Delta n2 \cdot \Delta T1 \tag{9}$$

If the CO concentration of the reformate gas flowing into the first PROX reactor 20A is Cin, and the first PROX reactor 20A and second PROX reactor 20B decrease the CO concentration Cin in the reformate gas to the CO concentration of 20 ppm in the outflowing gas, the following relation (10) between Cin, $\Delta n1$, $\Delta n2$ should be satisfied.

$$Cin \cdot (1-0.95-\Delta n1) \cdot (1-0.98-\Delta n2) = 0.002 \tag{10}$$

Cin is the concentration detected by the CO concentration sensor 11. Therefore, the increments $\Delta n1$, $\Delta n2$ in the CO conversion rate of the first PROX reactor 20A and second PROX reactor 20B can be calculated from the following equations (9), (10).

In the step S42, the controller 5 calculates the air flow rate supplied to the first PROX reactor 20A from the sum of the target CO conversion rate of 95% and increment $\Delta n1$ by looking up a map having the characteristics shown in FIG. 3 prestored in the memory. The controller 5 further adjusts the opening of the valve 7 so that the calculated air flow rate is realized.

In the next step S36, in an identical manner to that of the second embodiment, the CO concentration in the gas flowing into the second PROX reactor 20B is calculated.

In the next step S43, the air flow rate supplied to the second PROX reactor 20B is likewise calculated from the sum of the target CO conversion rate of 98% and increment Δn2 by looking up a map having the characteristics shown in FIG. 3. The controller 5 further adjusts the opening of the valve 8 so that the calculated air flow rate is realized. After the processing of the step S43, the controller 5 terminates the routine.

According to this embodiment, the air flow rate supplied to the PROX reactors is increased according to the differences ΔT1, ΔT2 between the upper limiting temperatures for catalyst activation and the catalyst temperatures of the PROX reactors, so the CO concentration can be efficiently reduced by using all the temperature differences between the upper limiting temperatures for catalyst activation and the catalyst temperatures of the PROX reactors.

On the other hand, due to the steps S33, S34, when either one of the catalyst temperatures of the PROX reactors is not less than the upper limiting temperatures for catalyst activation, the air flow rate supplied to the corresponding PROX reactor(s) can be reduced, so transient increase of the catalyst temperatures of the PROX reactors can be prevented as in the first and second embodiments.

Figure 7:
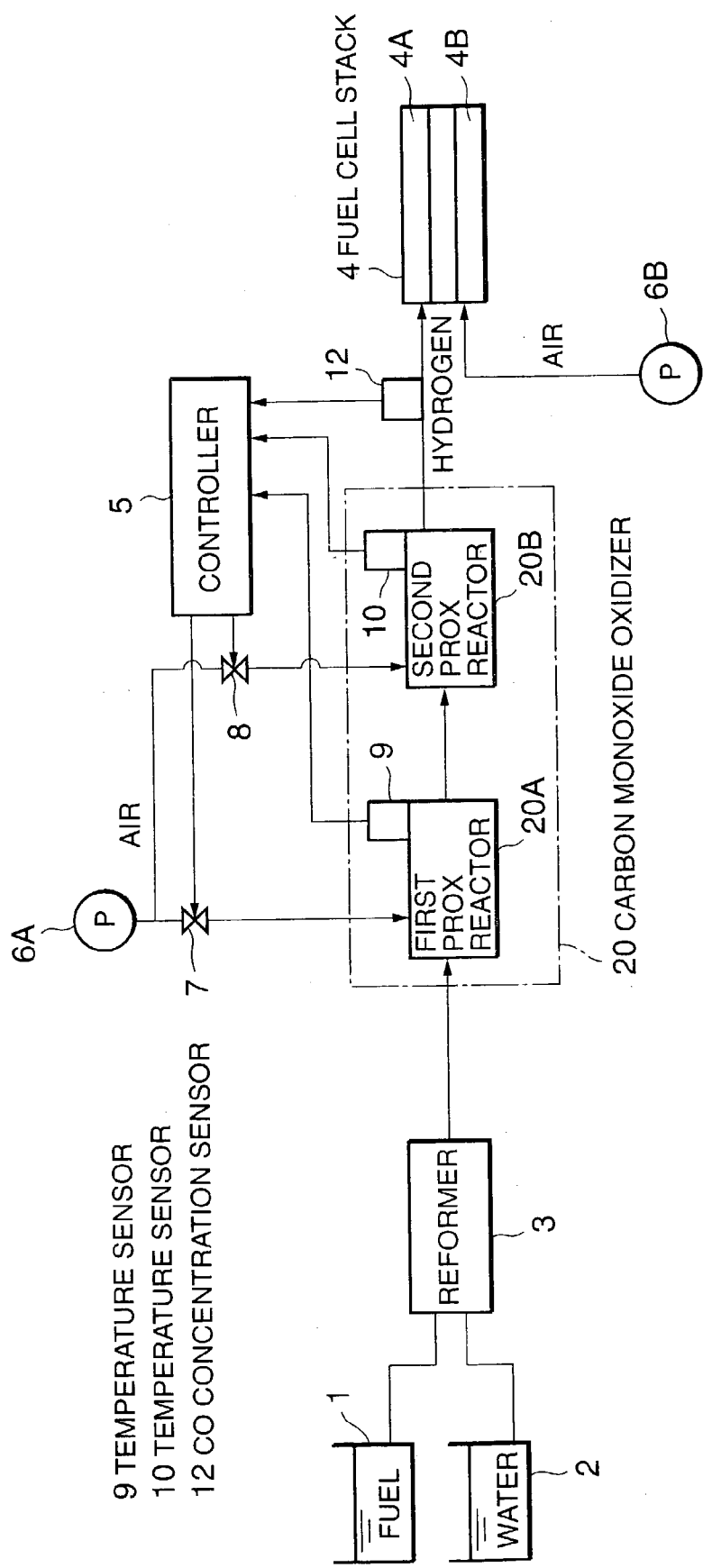
FIG. 7 is a schematic diagram of a fuel cell power plant using a carbon monoxide removal system according to a fourth embodiment of this invention.

Next, referring to FIGS. 7, 8, a fourth embodiment of this invention will be described.

According to this embodiment, the hardware construction is different from that of the first-third embodiments.

Specifically, in this embodiment, instead of the CO concentration sensor 11 which detects the CO concentration in the reformate gas generated by the reformer 3, a concentration sensor 12 which detects the CO concentration in the hydrogen-rich gas supplied to the fuel cell stack 4 from the second PROX reactor 20B is provided. The remaining features of the hardware are identical to those of the first-third embodiments.

Figure 8:
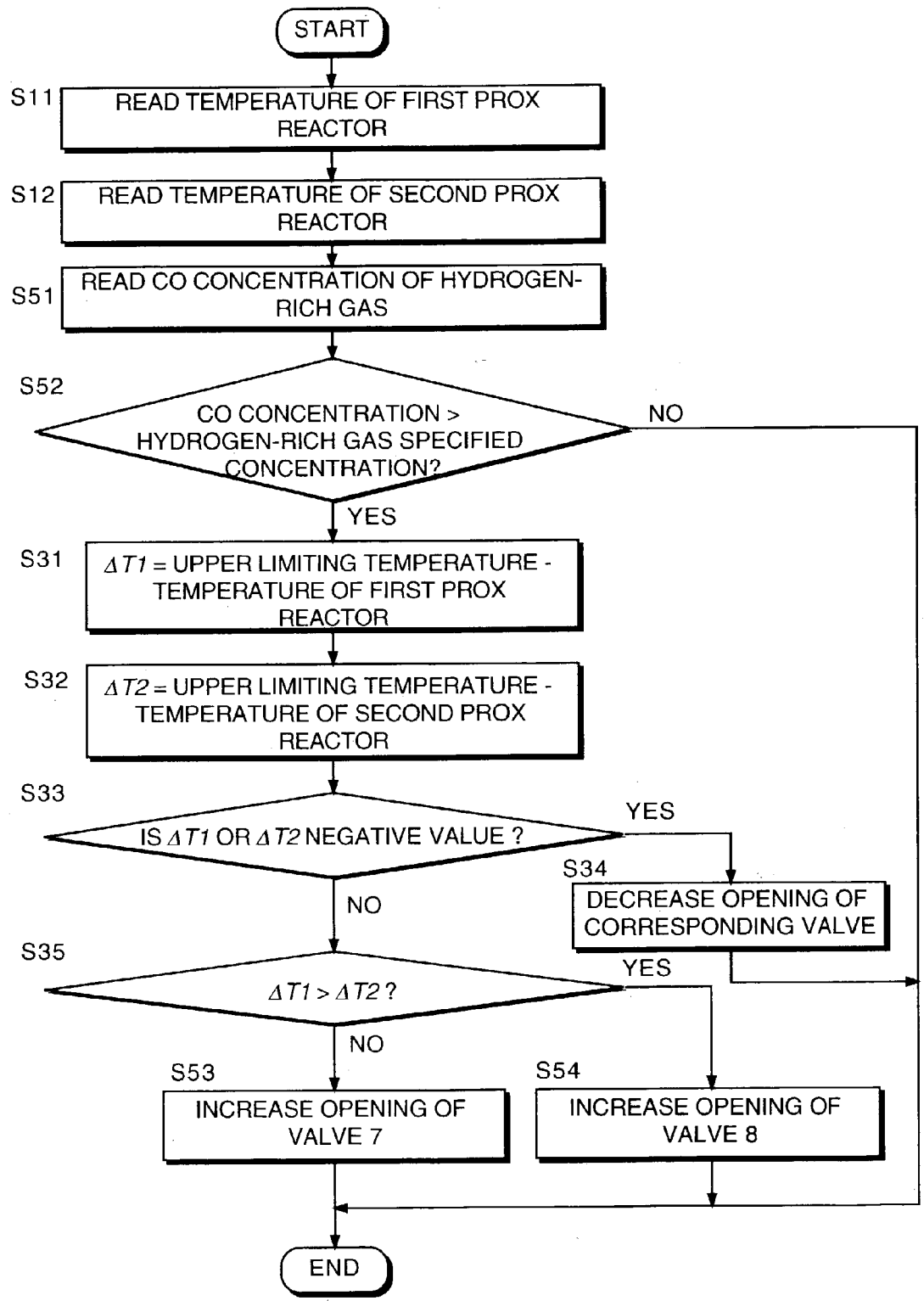
FIG. 8 is similar to FIG. 2, but showing the fourth embodiment of this invention.

According to this embodiment, the controller 5 executes a routine for controlling the air supply flow rate shown in FIG. 8. In this routine, the processing of the steps S11, S12, S31–S35 is identical to that of the routine of FIG. 5 of the second embodiment.

Referring to FIG. 8, the controller 5, in the step S11, reads the temperature detected by the temperature sensor 9, in, the step S12, reads the temperature detected by the temperature sensor 10, and in a step S51, reads the CO concentration of the hydrogen-rich gas detected by the concentration sensor 12.

In a following step S52, the CO concentration of the hydrogen-rich gas and a hydrogen-rich gas specified concentration are compared. The hydrogen-rich gas specified concentration is the upper limiting value of the CO concentration which does not affect the power generating performance of the fuel cell stack 4. Typically, the specified concentration of the hydrogen-rich gas is 30 ppm. If the CO concentration of the hydrogen-rich gas is lower than the specified concentration, the controller 5 does not proceed to subsequent steps, and immediately terminates the routine. If the CO concentration of the hydrogen-rich gas is not lower than the specified concentration, the controller 5 performs the processing of the steps S31–S35 which were described in relation to the second embodiment.

In the step S35, when the temperature difference ΔT1 is larger than the temperature difference ΔT2, the controller 5, in a step S53, increases the opening of the valve 7 so that the air flow rate supplied by the valve 7 increases by a fixed amount. On the other hand, when the temperature difference ΔT1 is not larger than the temperature difference ΔT2, the controller 5, in a step S54, increases the opening of the valve 8 so that the air flow rate supplied to the valve 8 increases by a fixed amount.

After the processing of the steps S53 or S54, the controller 5 terminates the routine.

According to this embodiment, if the CO concentration of the hydrogen-rich gas supplied to the fuel cell stack 4 is not lower than the hydrogen-rich specified concentration, the controller 5 increases the air flow rate supplied to one of the PROX reactors according to the temperature differences ΔT1, ΔT2, and repeats this operation until the CO concentration of the hydrogen-rich gas falls to the hydrogen-rich gas specified concentration. In other words, the air flow rate supplied to the PROX reactors 20A, 20B is feedback-controlled based on the CO concentration of the hydrogen-rich gas.

The CO conversion rate of the first PROX reactor 20A and second PROX reactor 20B are not necessarily constant due to temperature variation and catalyst deterioration. However, if the air flow rate supplied is feedback-controlled based on the CO concentration of the hydrogen-rich gas, the CO concentration of the hydrogen-rich gas can always be suppressed below the hydrogen-rich gas specified concentration even if there is scatter in the performance of the PROX reactors 20A, 20B.

According to this embodiment, the air flow rate supplied is increased to whichever of the PROX reactors has the higher tolerance for increase of catalyst temperature, so temperature rise above the upper limiting temperature for catalyst activation due to the increase of air flow rate can effectively be prevented.

Next, referring to FIG. 9, a fifth embodiment of this invention will be described.

The hardware construction of this embodiment is identical to that of the fourth embodiment. In this embodiment, only the routine for controlling the air supply flow rate executed by the controller 5 is different from the fourth embodiment.

Figure 9:
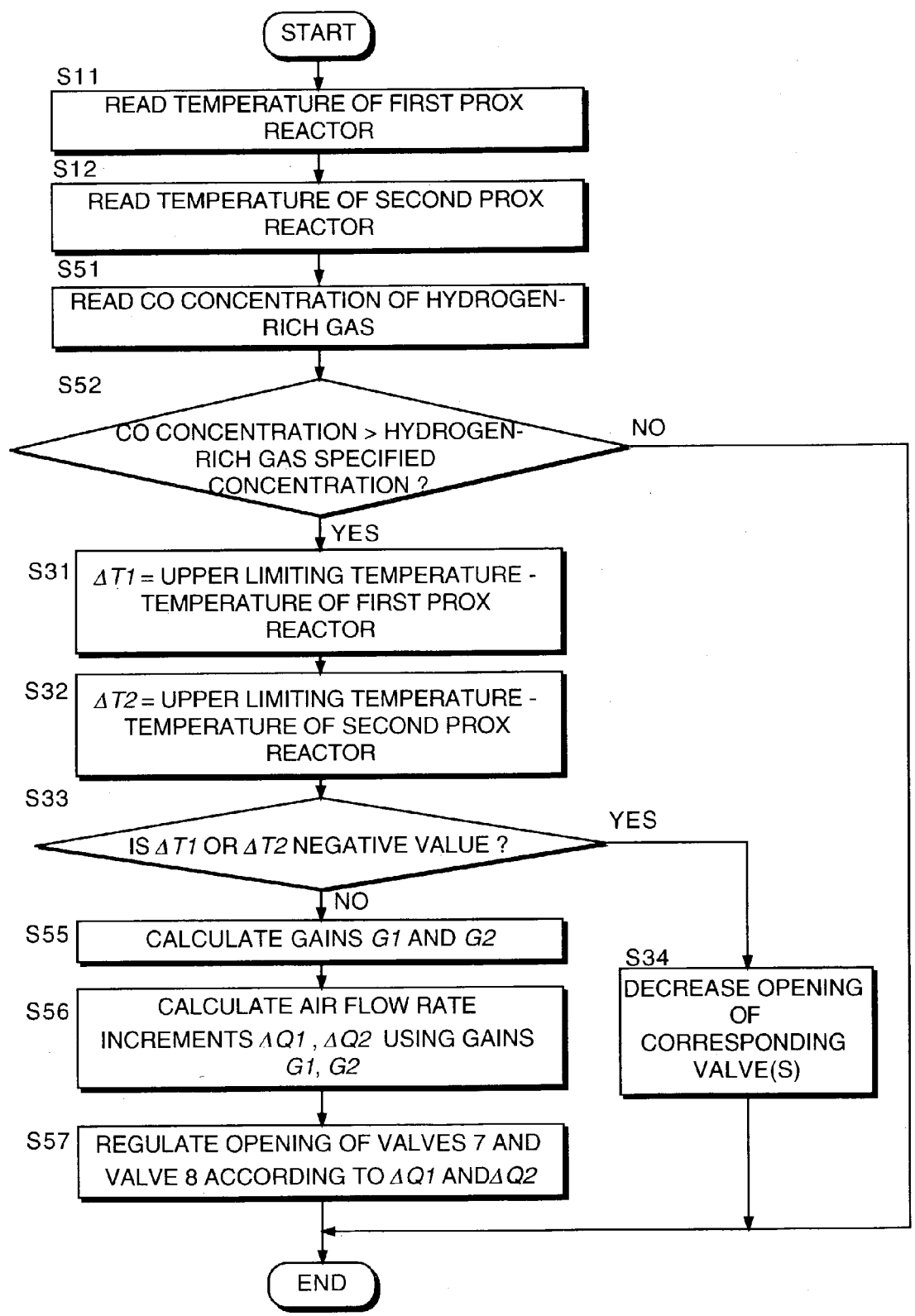
FIG. 9 is similar to FIG. 2, but showing a fifth embodiment of this invention.
Figure 10:
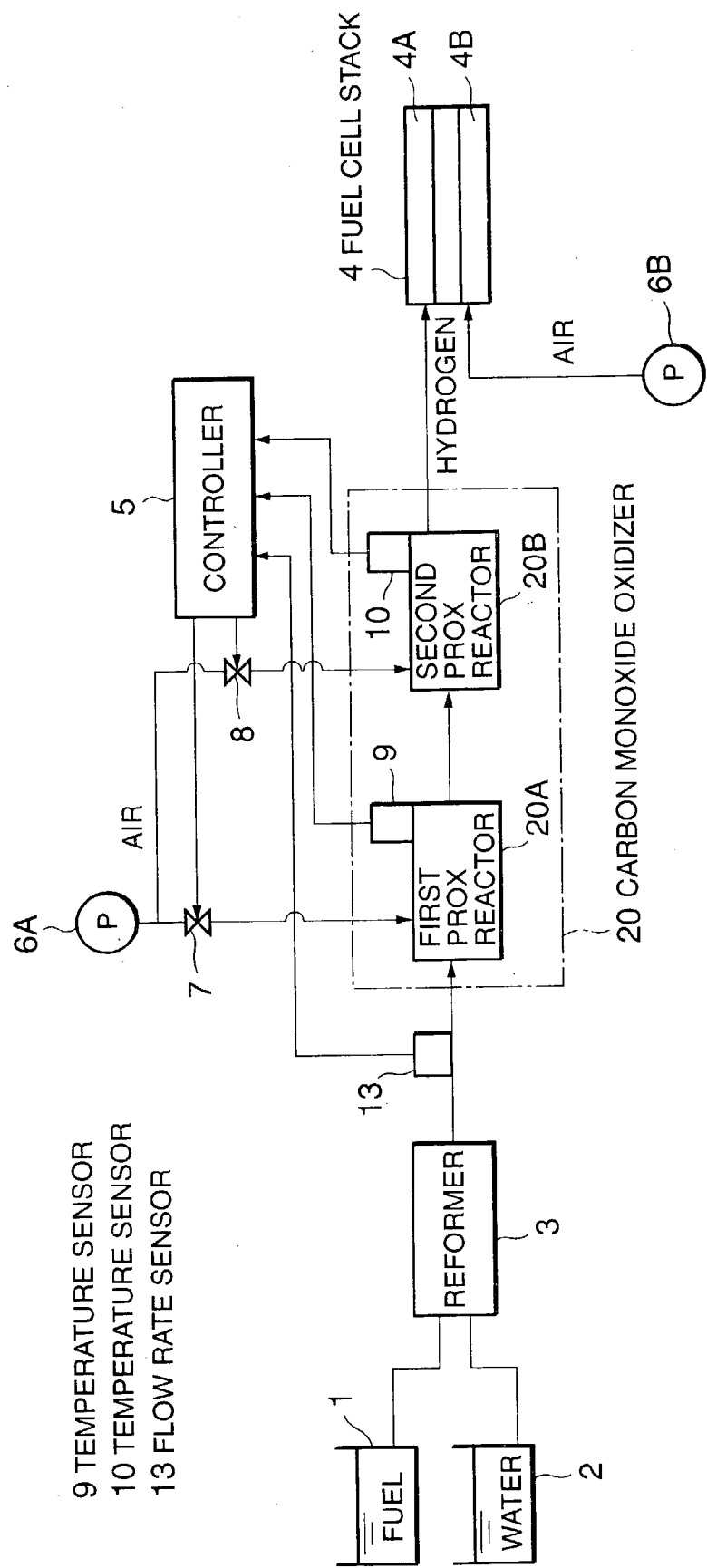
FIG. 10 is a schematic diagram of a fuel cell power plant using a carbon monoxide removal system according to a sixth embodiment of this invention.

Referring to FIG. 9, the processing of the steps S11, S12, steps S51, S52 and steps S31–S34 of this routine are identical to the routine of FIG. 8 in the fourth embodiment. In this routine, the method of feedback-controlling the air flow rate supplied to the PROX reactors 20A, 20B based on the CO concentration of the hydrogen-rich gas, is different from that of the fourth embodiment.

In the fourth embodiment, of the two PROX reactors 20A, 20B, only the air flow rate supplied to the reactor having the larger temperature difference is increased by a fixed increment, but according to this embodiment, the air flow rates supplied to the PROX reactors 20A, 20B are both increased, and gains G1, G2 applied to the calculation of the increase amount of the air supply flow rate are made to vary dynamically according to the temperature differences ΔT1, ΔT2. Specifically, in a step S55, the controller 5 determines the ratio of the air increase amount gains G1, G2 according to the temperature differences ΔT1, ΔT2 by the following equation (11).

$$G1 \Delta T2 = G2 \cdot \Delta T1 \tag{11}$$

Herein, the sum value of the air increase amount gains G1, G2 is fixed, and this sum value is first determined by experiment or simulation. The values of the air increase amount gains G1, G2 are determined from this sum value and the ratio of the air increase amount gains G1, G2 obtained from equation (11).

In a following step S56, the controller 5 calculates an increment ΔQ1 of the air supply flow rate to the first PROX reactor 20A by multiplying a first basic increment for the first PROX reactor 20A by the air increase amount gain G1. Likewise, an increment ΔQ2 of the air supply flow rate to the second PROX reactor 20B is calculated by multiplying a second basic increment for the second PROX reactor 20B by the air increase amount gain G2. The first basic increment and second basic increment are fixed values predetermined by experiment or simulation.

In a next step S57, the opening of the valve 7 is adjusted based on the increment $\Delta Q1$ of the air supply flow rate to the first PROX reactor 20A, and the opening of the valve 8 is adjusted based on the increment $\Delta Q2$ of the air supply flow rate to the second PROX reactor 20B.

Also in this embodiment, as in the fourth embodiment, the CO concentration in the hydrogen-rich gas can always be suppressed below the specified concentration even if there is scatter in the performance of the PROX reactors. Further, the air supply flow rate to the PROX reactors is increased according to the differences $\Delta T1$, $\Delta T2$ between the upper limiting temperature for catalyst activation and the catalyst temperatures of the PROX reactors, so the CO concentration can be efficiently reduced making use of all the temperature differences between the upper limiting temperature for catalyst activation and the catalyst temperatures of the PROX reactors.

Next, a sixth embodiment of this invention will be described referring to FIGS. 10, 11 and FIGS. 12A, 12B.

In this embodiment, the hardware construction is different from that of the first-third embodiments.

Specifically, in this embodiment, instead of the CO concentration sensor 11 which detects the CO concentration of reformate gas generated by the reformer 3 a flow rate sensor 13 which detects the flow rate of reformate gas generated by the reformer 12 is installed midway in the pipe leading reformate gas from the reformer 3 to the carbon monoxide oxidizer 20. The remaining features of the construction are identical to those of the first-third embodiments.

Figure 2:
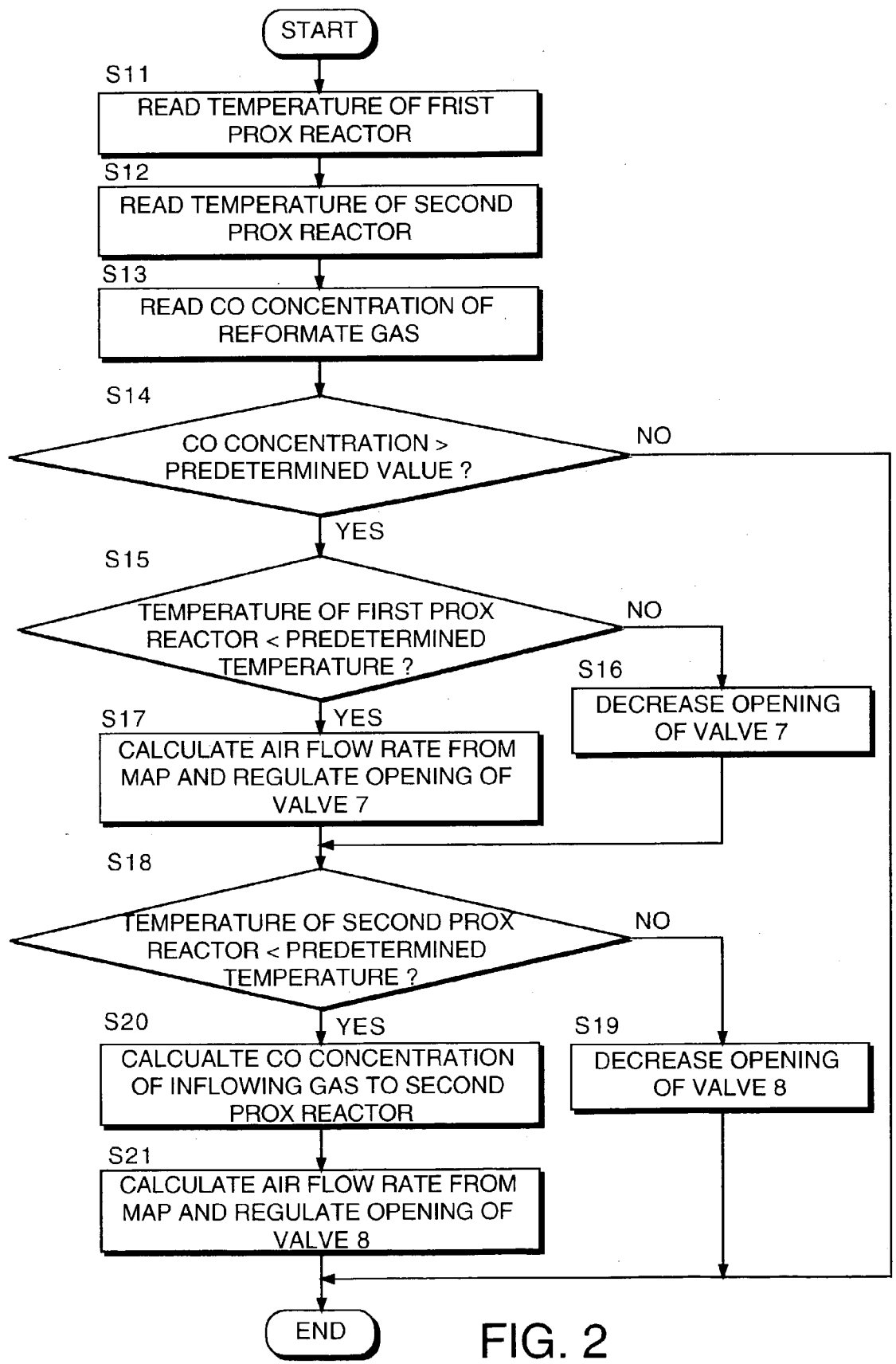
FIG. 2 is a flowchart describing a routine for controlling an air supply flow rate executed by a controller according to this invention.
Figure 11:
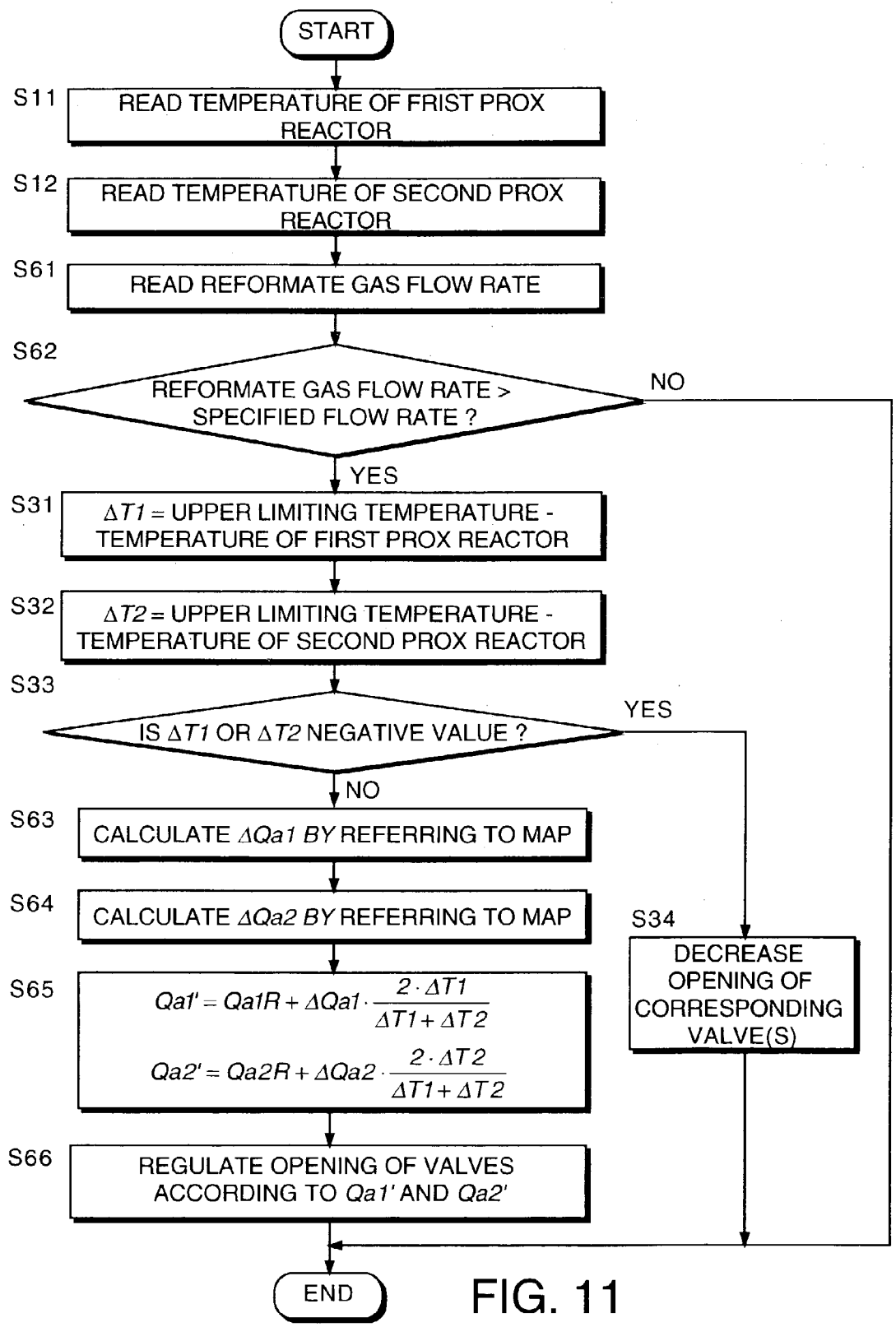
FIG. 11 is similar to FIG. 2, but showing the sixth embodiment of this invention.

In this embodiment, instead of the routine of FIG. 2 in the first embodiment, the controller 5 executes a routine for controlling the air supply flow rate shown in FIG. 11. In this embodiment, the opening of the valves 7, 8 are first initialized to an opening corresponding to a specified flow rate of reformate gas.n Herein, the specified flow rate corresponds to a flow rate when the power plant is running steadily.

Referring to FIG. 11, the processing of the steps S11, S12 is identical to the routine of FIG. 2 of the first embodiment. The processing of the steps S31–S34 is identical to the routine of FIG. 5 of the second embodiment.

In a step S61 following the step S12, the controller 5 reads the reformate gas flow rate detected by the flow rate sensor 13.

In a next step S62, it is determined whether the reformate gas flow rate is equal to the specified flow rate. When the reformate gas flow rate is equal to the specified flow rate, the controller 5 immediately terminates the routine without preceding to subsequent steps.

Figure 4:
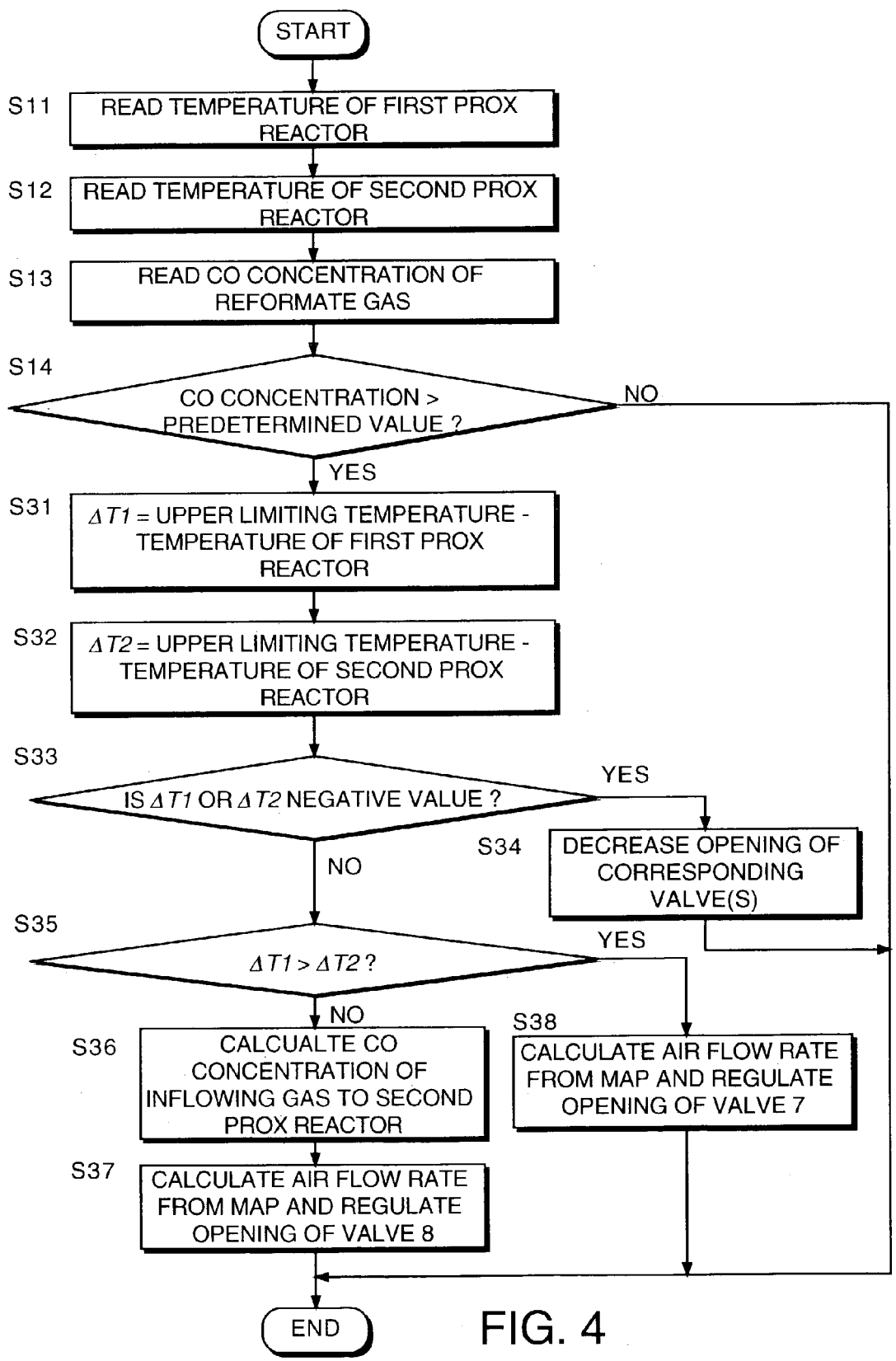
FIG. 4 is similar to FIG. 2, but showing a second embodiment of this invention.

When the reformate gas flow rate is not equal to the specified flow rate, the controller 5 performs the processing of the steps S31–S34 as in the routine of FIG. 4 of the second embodiment.

Figure 12A:
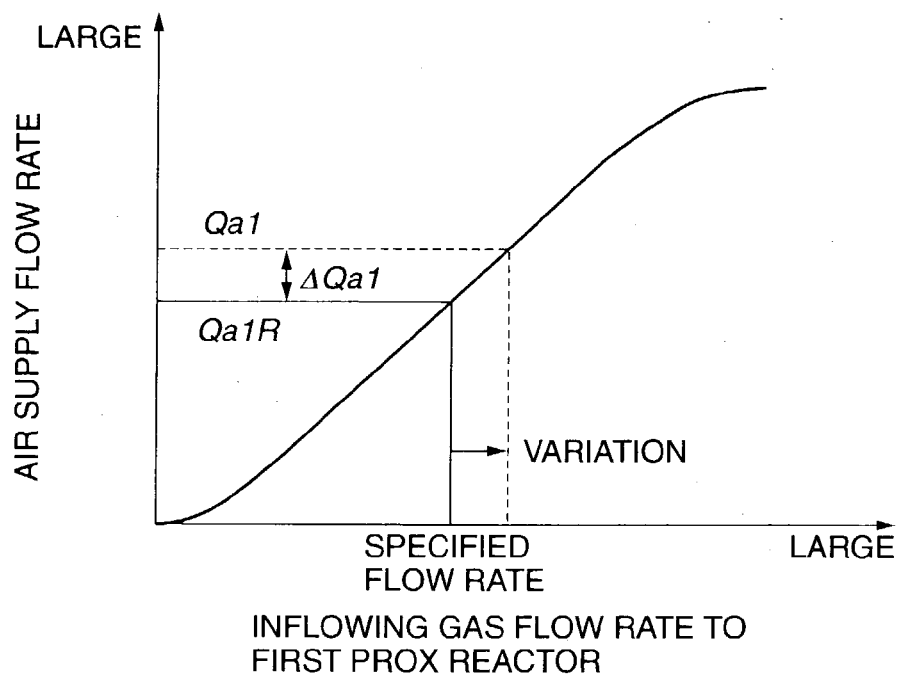
FIGS. 12A, 12B are diagrams describing the characteristics of a map specifying the relation between the flow rate of reformate gas flowing into the PROX reactors and the air amount supplied to the PROX reactors stored by the controller according to the sixth embodiment of this invention.

In the step S33, when neither of the temperature differences $\Delta T1$, $\Delta T2$ are not negative values, in a step S63, the controller 5 calculates a basic variation amount $\Delta Qa1$ of the air flow rate supplied to the first PROX reactor 20A from the reformate gas flow rate by looking up a map having the characteristics shown in FIG. 12A which is prestored in the memory. Referring to FIG. 12A, the basic variation amount $\Delta Qa1$ in this map means the variation amount from a specified flow rate Qa1R of the air supply flow rate when the reformate gas flow rate increases as shown by the dotted line relative to the specified flow rate.

Figure 12B:
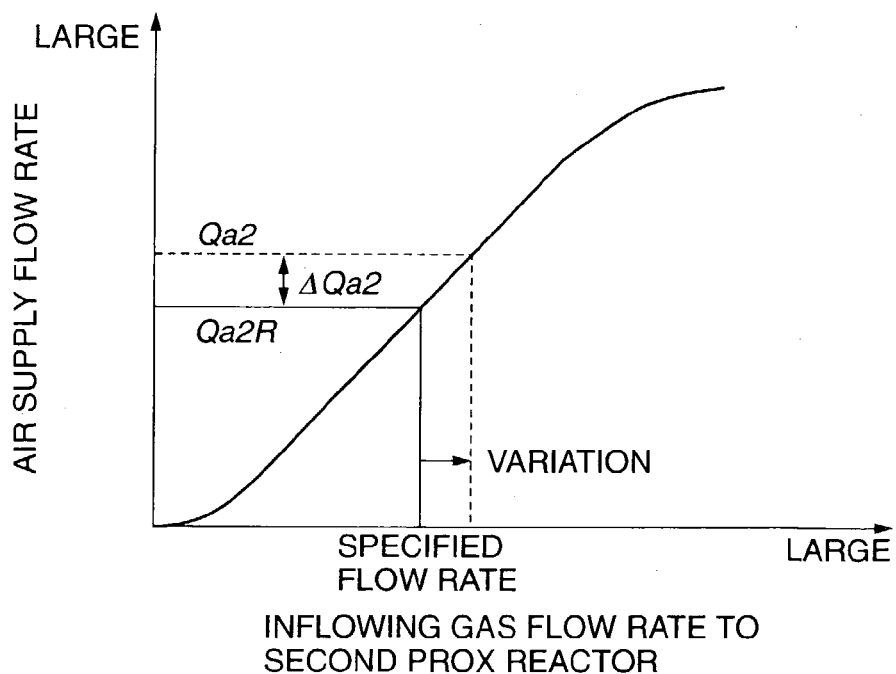

In a following step S64, the controller 5 calculates a basic variation amount $\Delta Qa2$ of the air flow rate supplied to the second PROX reactor 20B from the gas flow rate flowing into the second PROX reactor 20B by looking up a map having the characteristics shown in FIG. 12B which is prestored in the memory. Herein, the gas flow rate flowing into the second PROX reactor 20B is the gas flow rate flowing out of the first PROX reactor 20A, and this may be approximated to the sum of the reformate gas flow rate flowing into the first PROX reactor 20A and the air flow rate supplied to the first PROX reactor 20A.

Referring to FIG. 12B, the basic variation amount $\Delta Qa2$ in this map is the variation amount from the specified flow rate of the air supply flow rate when the inflowing gas flow rate increases as shown by the dotted line relative to the specified flow rate.

In a next step S65, the controller 5 calculates an air flow rate Qa1' supplied to the first PROX reactor 20A and an air flow rate Qa2' supplied to the second PROX reactor 20B by applying the following equations (12), (13).

$$Qa1' = Qa1R + \Delta Qa1 \cdot \frac{2 \cdot \Delta T1}{\Delta T1 + \Delta T2} \qquad (12)$$

$$Qa2' = Qa2R + \Delta Qa2 \cdot \frac{2 \cdot \Delta T2}{\Delta T1 + \Delta T2} \qquad (13)$$

In a next step S66, the opening of the valve 7 is adjusted so that the air flow rate Qa1' is realized, and the opening of the valve 8 is adjusted so that the air flow rate Qa2' is realized. After the processing of the step S66, the controller 5 terminates the routine.

In FIGS. 12A, 12B, it was assumed that the basic variation amounts $\Delta Qa1$, $\Delta Qa2$ were positive values, but when the reformate gas flow rate has decreased from the specified flow rate, the basic variation amounts $\Delta Qa1$, $\Delta Qa2$ become negative values. As can be seen from equations (12), (13), in this case, the air flow rate Qa1' is a smaller value than the specified air flow rate Qa1R, and the air flow rate Qa2' is a smaller value than the specified air flow rate Qa2R.

If the catalyst temperature of one of the first PROX reactor 20A and second PROX reactor 20B is not less than the upper limiting temperature for catalyst activation, the opening of the valves 7 or 8 is decreased as in all the other embodiments, so that the air flow rate supplied to the corresponding first PROX reactor 20A or second PROX reactor 20B is decreased. Therefore, the carbon monoxide removal performance can be optimized while preventing catalyst temperature rise of the PROX reactors.

Figure 13:
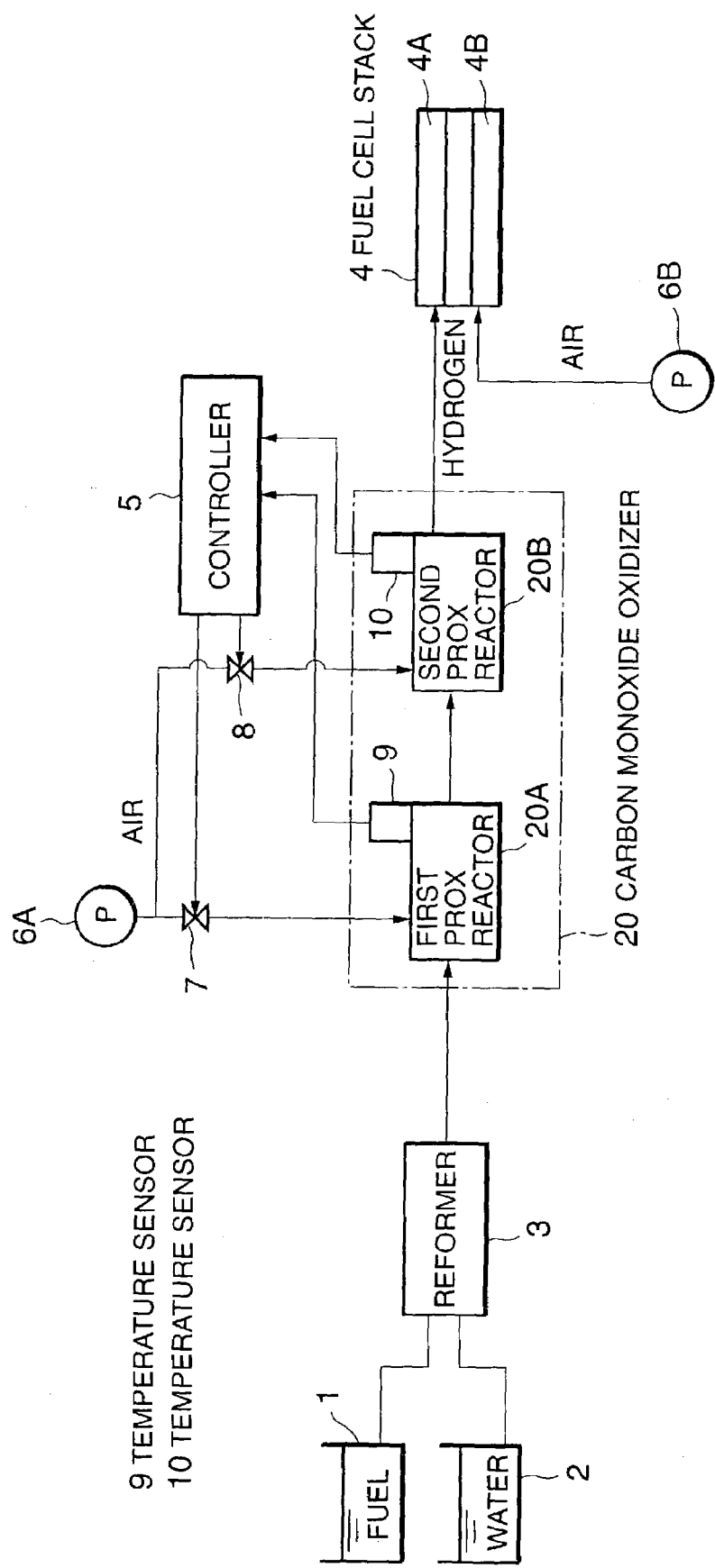
FIG. 13 is a schematic diagram of a fuel cell power plant using a carbon monoxide removal system according to a seventh embodiment of this invention.

Next, referring to FIGS. 13, 14, a seventh embodiment of this invention will be described.

This embodiment is different from the other embodiments in terms of the hardware construction. Referring to FIG. 13, according to this embodiment, the CO concentration sensor or flow rate sensor is not used. According to this embodiment, when the fuel cell power plant is running steadily, it is assumed that the CO concentration and flow rate of reformate gas are respectively constant.

Figure 14:
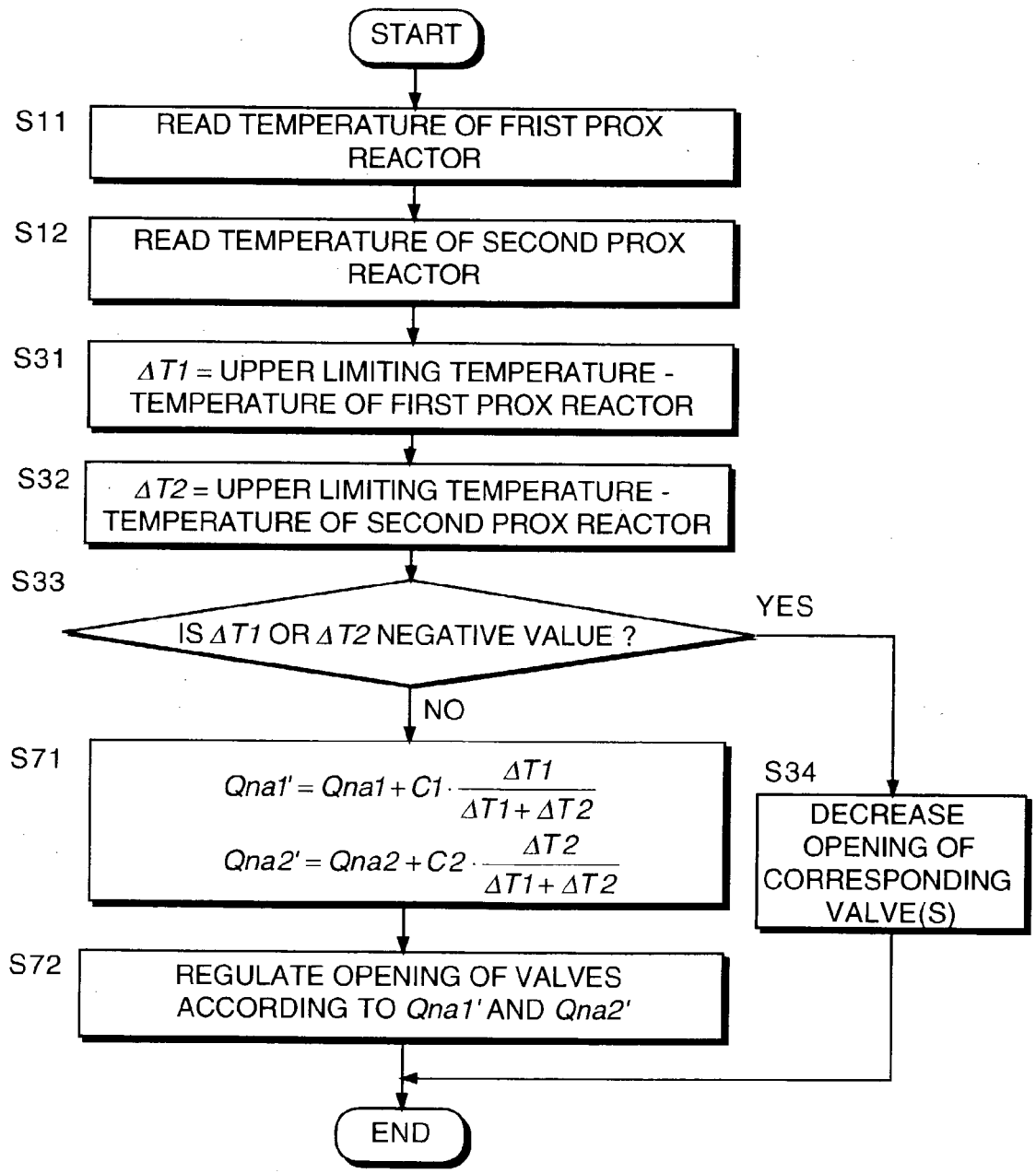
FIG. 14 is similar to FIG. 2, but showing the seventh embodiment of this invention.

Instead of the routine of FIG. 2 of the first embodiment, the controller 5 executes a routine for controlling the supply air flow rate shown in FIG. 14.

The processing of the steps S11, S12 is identical to the routine of FIG. 2 according to the first embodiment. The processing of the steps S31–S34 is identical to the routine of FIG. 4 according to the second embodiment.

In steps S63, S64, when both of the temperature differences $\Delta T1$, $\Delta T2$ are not negative values, the controller 5, in a step S71, applies the following equations (14), (15), and calculates the air supply flow rate Qna1' to the first PROX reactor 20A and the air supply flow rate Qna2' to the PROX reactor 20B from the temperature differences $\Delta T1$, $\Delta T2$.

$$Qna1' = Qna1 + C1 \cdot \frac{\Delta T1}{\Delta T1 + \Delta T2} \qquad (14)$$

where, Qna1=specified air flow rate supplied to the first PROX reactor 20A, and
C1=correction coefficient.

$$Qna2' = Qna2 + C2 \cdot \frac{\Delta T2}{\Delta T1 + \Delta T2} \qquad (15)$$

where, Qna2=specified air flow rate supplied to the second PROX reactor 20B, and
C2=correction coefficient.

The correction coefficients C1, C2 are respectively set experimentally.

In a following step S72, the controller 5 adjusts the opening of the valve 7 so that the calculated air flow rate Qna1' is realized, and adjusts the opening of the valve 8 so that the calculated air flow rate Qna2' is realized. After the processing of the step S72, the controller 5 terminates the routine.

In this embodiment also, the air supply flow rate to the PROX reactor having a higher tolerance for temperature rise is increased based on the catalyst temperatures of the first PROX reactor 20A and second PROX reactor 20B, so excessive catalyst temperature rise can be prevented, and the carbon monoxide removal performance of the of the first PROX reactor 20A and second PROX reactor 20B can be utilized to the maximum.

In this embodiment, the CO concentration sensor or flow rate sensor is not used, so the construction of the device can be simplified.

The contents of Tokugan 2002-88058, with a filing date of Mar. 27, 2002 in Japan, are hereby incorporated by reference.

Although the invention has been described above by reference to certain embodiments of the invention, the invention is not limited to the embodiments described above. Modifications and variations of the embodiments described above will occur to those skilled in the art, in light of the above teachings.

For example, in all the aforesaid embodiments, the carbon monoxide oxidizer 20 is comprised of the two PROX reactors 20A, 20B, but this invention may be applied also to a carbon monoxide removal device comprising three or more PROX reactors.

The embodiments of this invention in which an exclusive property or privilege is claimed are defined as follows:

What is claimed is:

1. A carbon monoxide removal system comprising:
    plural preferential oxidation reactors disposed in series which remove carbon monoxide contained in reformate gas via a catalyst, the preferential oxidation reactors comprising a first preferential oxidation reactor and a second preferential oxidation reactor arranged further downstream than the first preferential oxidation reactor;
    an air supply mechanism which supplies air containing oxygen as an oxidizing agent to the first preferential oxidation reactor and the second preferential oxidation reactor;
    a first temperature sensor which detects a temperature of the first preferential oxidation reactor;
    a second temperature sensor which detects a temperature of the second preferential oxidation reactor; and
    a controller functioning to:
        determine a target carbon monoxide conversion rate of the first preferential oxidation reactor based on the temperature of the first preferential oxidation reactor;
        determine a target carbon monoxide conversion rate of the second preferential oxidation reactor based on the temperature of the second preferential oxidation reactor;
        control the air supply mechanism so that an air supply flow rate to the first preferential oxidation reactor based on the target carbon monoxide conversion rate of the first preferential oxidation reactor, and an air supply flow rate to the second preferential oxidation reactor based on the target carbon monoxide conversion rate of the second preferential oxidation reactor.

2. The carbon monoxide removal system as defined in claim 1, wherein the controller further functions to:
    calculate a difference between an upper limiting temperature for catalyst activation and the temperature of the first preferential oxidation reactor as a first temperature difference;
    calculate a difference between the upper limiting temperature for catalyst activation and the temperature of the second preferential oxidation reactor as a second temperature difference;
    calculate the target carbon monoxide conversion rate of the first preferential oxidation reactor and the target carbon monoxide conversion rate of the second preferential oxidation reactor by respectively increasing a preset target carbon monoxide conversion rate of the first preferential oxidation reactor and a preset target carbon monoxide conversion rate of the second preferential oxidation reactor according to a ratio of the first temperature difference and the second temperature difference.

3. The carbon monoxide removal system as defined in claim 2, wherein the carbon monoxide removal system further comprises a carbon monoxide sensor which detects a carbon monoxide concentration of the reformate gas flowing into the first preferential oxidation reactor, and the controller further functions to:
    calculate the target carbon monoxide conversion rate of the first preferential oxidation reactor and the target carbon monoxide conversion rate of the second preferential oxidation reactor based on the carbon monoxide concentration of the reformate gas flowing into the first preferential oxidation reactor.

4. The carbon monoxide removal system as defined in claim 3, wherein the controller further functions to:
    calculate a target air supply flow rate to the first preferential oxidation reactor from the carbon monoxide concentration of the reformate gas flowing into the first preferential oxidation reactor and the target carbon monoxide conversion rate of the first preferential oxidation reactor;
    calculate a carbon monoxide concentration of an inflowing gas into the second preferential oxidation reactor based on the target carbon monoxide conversion rate of the first preferential oxidation reactor and the carbon monoxide concentration of the reformate gas flowing into the first preferential oxidation reactor;

calculate a target air supply flow rate to the second preferential oxidation reactor from the carbon monoxide concentration of the inflowing gas into the second preferential oxidation reactor and the target carbon monoxide conversion rate of the second preferential oxidation reactor; and control the air supply mechanism so that the air supply flow rate to the first preferential oxidation reactor coincides with the target air supply flow rate to the first preferential oxidation reactor and the air supply flow rate to the second preferential oxidation reactor coincides with the target air supply flow rate to the second preferential oxidation reactor.

5. The carbon monoxide removal system as defined in claim 2, wherein the controller further functions to:

calculate the target carbon monoxide conversion rate of the first preferential oxidation reactor by adding a first increment to the preset target carbon monoxide conversion rate of the first preferential oxidation reactor; and calculate the target carbon monoxide conversion rate of the second preferential oxidation reactor by adding a second increment to the preset target carbon monoxide conversion rate of the second preferential oxidation reactor;

wherein, the ratio of the first increment with respect to the second increment is set equal to the ratio of the first temperature difference with respect to the second temperature difference.

6. The carbon monoxide removal system as defined in claim 1, wherein the controller further functions to:

calculate a difference between a predetermined upper limiting temperature for catalyst activation and the catalyst temperature of the first preferential oxidation reactor as a first temperature difference;

calculate a difference between the predetermined upper limiting temperature for catalyst activation and the catalyst temperature of the second preferential oxidation reactor as a second temperature difference;

determine whether or not one of the first temperature difference and the second temperature difference is a negative value; and when one of the first temperature difference and the second temperature difference is a negative value, control the air supply mechanism to decrease the air supply flow rate to the corresponding preferential oxidation reactor.

7. The carbon monoxide removal system as defined in claim 1, wherein the controller further functions to:

increase the target carbon monoxide conversion rate of the first preferential oxidation reactor as the temperature of the first preferential oxidation reactor becomes lower; and increases the target carbon monoxide conversion rate of the second preferential oxidation reactor as the temperature of the second preferential oxidation reactor becomes lower.

* * * * *